United States Patent [19]

Mehta et al.

[11] Patent Number: 5,216,028
[45] Date of Patent: Jun. 1, 1993

[54] THERAPEUTIC USES OF A DIPHENYLSULFIDE COMPOUND TO TREAT DEPRESSION AND EFFECT SEROTONIN UPTAKE

[75] Inventors: Nariman B. Mehta, Leesburg, Fla.; Lawrence E. Brieaddy, Raleigh, N.C.

[73] Assignee: Burroughs Wellcome Co., Research Triangle Park, N.C.

[21] Appl. No.: 725,863

[22] Filed: Jul. 3, 1991

Related U.S. Application Data

[63] Continuation-in-part of Ser. No. 533,613, Jun. 5, 1990, Pat. No. 5,095,039.

[30] Foreign Application Priority Data

Jun. 6, 1989 [GB] United Kingdom ............... 8912971

[51] Int. Cl.$^5$ .......................................... A61K 31/135
[52] U.S. Cl. .................................................. 514/653
[58] Field of Search ........................................ 514/653

[56] References Cited

U.S. PATENT DOCUMENTS

4,056,632 11/1977 Mehta et al. ..................... 514/646
4,194,009 3/1980 Molloy et al. ..................... 514/646

OTHER PUBLICATIONS

Benfield, et al., Drugs, 32: pp. 481-508, (1986), Fluoxetine—A Review of Its Pharmacodynamic and Pharmacokinetic Properties, and Therapeutic Efficacy in Despressive Illness.
Burrows, et al., J. Clin. Phychiatry, 49:8, (Suppl.), Aug. 1988, pp. 18-22, Clinical Effects of Serotonin Reuptake Inhibitors in the Treatment of Depressive Illness.
Ferris, et al., The Journal of Pharmacology and Experimental Therapeutics, vol. 181, No. 3, 1972, pp. 407-416, A Comparison of the Capacities of Isomers of Amphetamine, Deoxypipradrol and Methylphenidate of Inhibit the Uptake of Tritiated Catecholamines into Rat Cerebral Cortex, Hypothalamus and Striatum and into Adrenergic Nerves of Rabbit Aorta.
Patrick, et al., The Journal of Pharmacology and Experimental Therapeutics, vol. 241, No. 1, 1987, pp. 152-158, Pharmacology of the Enantiomers of Threo-Methylphenidate.
Bondinell, et al., J. Med. Chem., 1980, 23, pp. 506-511, Inhibitors of Phenylethanolamine N-Methyltrasferase and Epinephrine Biosynthesis. 1. Chloro-Substituted 1,2,3,4-Tetrahydroisoquinolines.
Schindlbaure, Monatshefte fur Chemi, 99, pp. 1799-1807, (1968), Readtionen mit Dimethylformamid, 1. Mitt.

Primary Examiner—S. J. Friedman
Attorney, Agent, or Firm—Brown, Donald; Larry Nielsen; Hannah O. Green

[57] ABSTRACT

A halogen-substituted diphenylsufide compound is disclosed which produce a large selective inhibition of serotonin uptake in brain. This compound is useful in the treatment of depression as well as anxiety, obsessive compulsive disorders and alcoholism.

15 Claims, No Drawings

THERAPEUTIC USES OF A DIPHENYLSULFIDE COMPOUND TO TREAT DEPRESSION AND EFFECT SEROTONIN UPTAKE

This application is a continuation-in-part of U.S. Ser. No. 07/533,613, filed on Jun. 5, 1990, now U.S. Pat. No. 5,095,039 issued Mar. 10, 1992.

The present invention relates to a 5-chloro-substituted diphenylsulfide, processes for its preparation, pharmaceutical formulations containing it, and its use in medicine, in particular, for the treatment of depression.

Certain 2-hydroxymethyl diphenylsulfides with antidepressant activity are disclosed in U.K. Patent Specification 1,561,072 (U.S. Pat. No. 4,056,632). Compounds which inhibit serotonin uptake are described in U.S. Pat. No. 4,194,009. The use of serotonin uptake inhibitors for treatment of depression is discussed by Benfield et al., *Drugs*, 32, 481 (1986) and Burrows et al., *J. Clin. Psychiatry*, 49 Suppl., 18 (1988).

The compound of the present invention is useful in the treatment of depression in mammals. It produces a surprising and large selective inhibition of serotonin uptake in brain. In the compound of formula (I), below, this serotonin uptake inhibition is unexpectedly and surprisingly better than the serotonin uptake inhibition produced by the corresponding non-halogen substituted compounds of U.S. Pat. No. 4,056,632.

In particular, the present invention is directed to the compound represented by formula (I),

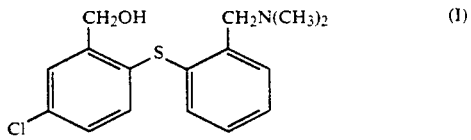

which is named 5-chloro-2-((2-((dimethylamino)methyl)phenyl)thio)-benzyl alcohol, and salts thereof.

Salts of this invention are preferably pharmaceutically acceptable acid addition salts. Examples of pharmaceutically acceptable acid addition salts of formula (I) are those prepared from e.g., hydrochloric, sulfuric, phosphoric, toluenesulfonic, methanesulfonic, acetic, maleic, fumaric, tartaric, citric, pamoic, succinic, and nitric acids. Salts of the invention also include those which may be used in intermediate process operations as well as those which are acceptable as final pharmaceutical products.

The compound of formula (I) is a serotonin uptake inhibitor as demonstrated by its ability to block the uptake of biogenic amines in rat synaptosomal preparations. The compound of formula (I) and pharmaceutically acceptable acid addition salts thereof are useful in the treatment of depression in mammals, including humans.

The present invention provides the compound of formula (I) or a pharmaceutically acceptable acid addition salt thereof for use in medicine. There is further provided the use of the compound of formula (I) or a pharmaceutically acceptable acid addition salt thereof in the manufacture of a medicament for treating depression. Additionally, there is provided a method of treating depression in humans which comprises administering to a patient an effective amount of the compound of formula (I) or a pharmaceutically acceptable acid addition salt thereof.

The compound of formula (I) may be synthesized by any method known in the art for making compounds of an analogous structure.

In particular, the compounds of formula (I) may be prepared as indicated in the following reaction scheme:

Step 1:

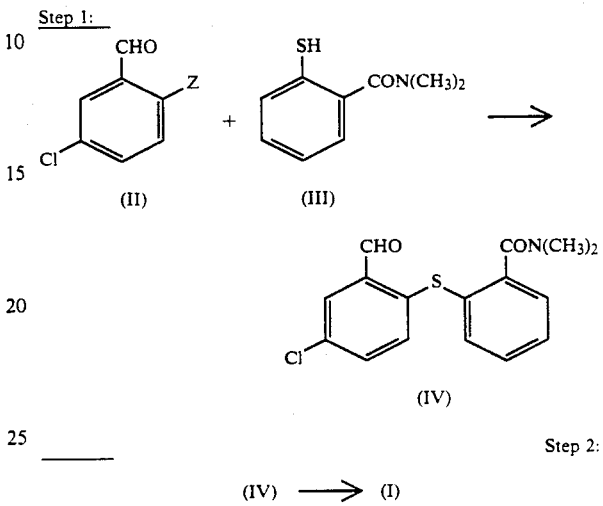

Step 2:

(IV) ⟶ (I)

where Z is a halogen. The reaction of Step 1, formation of the sulfide bridge, may be carried out in basic solution, for example, in potassium carbonate and a suitable solvent such as dimethylformamide, dimethylacetamide or dimethylsulfoxide, at a temperature in the range of 20° C. to 200° C.

Step 2 may be carried out by the reduction of a compound of formula (IV) with hydride reducing agents, for example diborane or lithium aluminum hydride at a temperature in the range of 20° C. to 70° C.

Compounds of formulas (II) and (III) may be prepared by methods well known in the art of organic chemistry from commercially available compounds.

Alternatively, the compound of formula (I) may be prepared by reaction of a compound of formula (V)

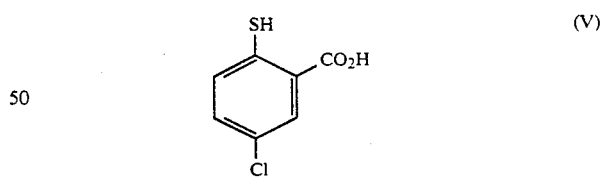

with a compound of formula (VI)

in the presence of an alkali metal lower alkoxide, for example, sodium methoxide, in dimethylformamide, followed by reduction, for example, with diborane or other hydride reducing agents, to form a compound of formula (VII)

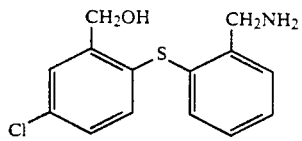

The compound of formula (VII) can then be converted to the compound of formula (I) by methods well known in the art of organic chemistry, for example by reaction with an aldehyde such as formaldehyde in the presence of acid, such as formic acid.

Acid addition salts may be prepared by reaction with an appropriate acid in a suitable solvent.

The compound of formula (I) and pharmaceutically acceptable acid addition salts thereof may be used in treating depression of three main types: neurotic or reactive depression with anxiety, somatic concern and tension; psychotic or endogenous depression with emotional withdrawal, motor retardation, blunted affect, guilt feelings and conceptual disorganization; and a group showing features of both neurotic and psychotic depression with hostility and suspiciousness. The compound of formula (I) and pharmaceutically acceptable acid addition salts thereof may also be used for the treatment of anxiety, obsessive compulsive disorders, and alcoholism.

The compound of this invention may be administered parenterally, orally, rectally, transdermally or topically. Parenteral administration includes subcutaneous, intramuscular and intravenous modes. Topical administration includes buccal and sublingual modes.

The preferred antidepressant dosage for parenteral administration of the compound of formula (I) (calculated as the base) is 0.5 mg/kg of mammal body weight per day, and the most preferred dosage is 1 mg/kg to 10 mg/kg of mammal body weight per day.

For the oral, rectal or topical mode of administration, the preferred antidepressant dosage of the compound of formula (I) (calculated as the base) is about 1 mg/kg to 50 mg/kg of mammal body weight per day, while the most preferred dosage (estimated as the base) is 1 mg/kg to 20 mg/kg of mammal body weight per day.

The compound of formula (I), or a pharmaceutically acceptable acid addition salt thereof, is preferably administered four times daily although the number of daily administrations of the medication and the total dose will vary according to the mammal being treated, and according to the exercise of the physician's discretion.

For example, for the treatment of depression in humans, the preferred unit dosage of the compound of formula (I) or a pharmaceutically acceptable acid addition salt thereof (calculated as the base) for oral or topical administration, or administration as a suppository, is about 1 mg to 200 mg, with the more preferred unit dosage being about 5 mg to 100 mg, and the most preferred unit dosage being about 10 mg to 50 mg. All the above doses are given in term of the weight of the compound of formula (I) in the form of its base, but as will be appreciated from the foregoing information, doses are preferably administered in the form of a pharmaceutically acceptable acid addition salt.

Preferred dosages for the treatment of anxiety, obsessive compulsive disorders and alcoholism are the same as dosages described above for treatment of depression.

The compound of formula (I) or pharmaceutically acceptable acid addition salts thereof (the active ingredients) are preferably administered in unit dosage form to the mammal being treated.

A pharmaceutical composition containing the compound of formula (I), or a pharmaceutically acceptable acid addition salt thereof, may be presented in discrete units such as tablets, capsules, lozenges, ampules (i.e., for injection), suppositories or liposomes each containing an effective antidepressant non-toxic amount of the compound and one or more pharmaceutically acceptable carriers.

The pharmaceutical compositions may be in the form of an oral unit dose preparation for example a cachet, tablet or capsule. Suitable pharmaceutically acceptable carriers for such compositions include solid diluents such as lactose, cornstarch, micronized silica gel, or merely the capsule shell as well as other excipients well known in the art for this purpose.

Compositions suitable for topical administration in the mouth, for example buccally or sublingually, include lozenges comprising the active compound in a flavored basis such as sucrose and acacia or tragacanth, and pastilles comprising the active compound in a basis such as gelatin and glycerin or sucrose and acacia.

The pharmaceutical compositions may further take the form of those suitable for rectal use as a suppository with the usual pharmaceutically acceptable carriers such as cocoa butter.

Pharmaceutical compositions for parenteral use include an ampule of a sterile solution or suspension with water or other pharmaceutically acceptable liquid as the carrier therefor, or an ampule of a sterile powder for dilution with a pharmaceutically acceptable liquid. Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved in an adhesive or 3) dispersed in a polymer. A suitable concentration of the active compound is about 1% to 20%, preferably about 3% to 15%. As one particular possibility, the active compound may be delivered from the patch by iontophoresis as generally described in *Pharmaceutical Research*, 3(6), 318 (1986).

It should be understood that in addition to the aforementioned ingredients, the pharmaceutical compositions of this invention may include one or more of additional ingredients such as diluents, buffers, flavoring agents, binders, surface active agents, thickeners, lubricants, preservatives, and the like. The compositions may be prepared by admixture of the ingredients, and, if necessary, shaping the resulting mass, and filling into suitable containers.

According to the present invention there is provided the compound of formula (I) and a pharmaceutically acceptable acid addition salt thereof.

According to the present invention, in yet another aspect, there are provided methods of synthesizing the compound of formula (I) comprising the application of known methods and those specified above for the preparation of the compound of formula (I) or acid addition salts thereof.

According to the present invention, in yet another aspect, there is provided a pharmaceutical composition, preferably in unit dosage form, comprising the compound of formula (I), or a pharmaceutically acceptable acid addition salt thereof, together with a pharmaceutically acceptable carrier.

According to still a further aspect of the present invention, there is provided a method of treating a depressed state in mammals, including humans, which comprises the administration of an antidepressant effective non-toxic amount (dose), preferably in a unit dosage form, of a compound of formula (I) or a pharmaceutically acceptable acid addition salt thereof. Conveniently the compound of formula (I) or its acid addition salt comprises from 5 to 95% by weight of the composition.

The following examples are provided by way of an illustration of the present invention and should in no way constitute a limitation thereof.

EXAMPLE 1

Preparation of 2-((4-Chloro-2-formylphenyl)thio)-N,N-dimethylbenzamide

Potassium carbonate (27.6 g) was added to a solution of 2,5-dichlorobenzaldehyde (30.2 g) (Bondinell et al., *J. Med. Chem.*, 23(5), 506 (1980)) and 2-thio-N,N-dimethylbenzamide (Schindlbauer, *Monatsh. Chem.*, 99(5), 1799 (1968)) (36.3 g) in 500 mL of dimethylformamide. The reaction mixture was stirred at 160° C. for four hours, added to 2.5 liters of chilled water and extracted with EtOAc to give 50.2 g of a tan solid. Recrystallization from acetone/hexane mixtures gave 43.5 g (80% yield) of 2-((4-chloro-2-formylphenyl)thio)-N,N-dimethylbenzamide, m.p. 87°–88° C.

Anal. Calcd. for $C_{16}H_{14}ClNO_2S$: C, 60.09; H, 4.41; N, 4.38; S, 10.03. Found: C, 60.16; H, 4.42; N, 4.36; S, 9.97.

EXAMPLE 2

Preparation of 5-Chloro-2-((2-((dimethylamino)methyl)-phenyl)thio)-benzyl Alcohol 2-((4-Chloro-2-formylphenyl)thio)-N,N-dimethylbenzamide (10.0 g) was dissolved in 80 mL of anhydrous tetrahydrofuran and, under nitrogen, added to 80 mL of 1.0M diborane at room temperature. The reaction mixture was refluxed for 2 hr and then stirred at room temperature for 17 hr. The reaction mixture was treated with 100 mL of 50% HCl, warmed on a steam bath for 1 hr and concentrated in vacuo. Treatment with solid NaOH and extraction with EtOAc gave the free base as a yellow oil. The base was dissolved in diethyl ether and acidified with ethereal HCl. The hydrochloride salt was recrystallized from MeOH/EtOAc mixtures to give 7.4 g (70% yield) of 5-chloro-2-((2-((dimethylamino)methyl)phenyl)thio)benzyl alcohol hydrochloride, m.p. 176°–177° C.

$^1$H NMR ($Me_2SO-d_6$) δ 10.98 (s, 1, NH), 6.96–7.93 (m, 7H, aromatic), 5.60 (s, 1, OH), 4.54 (s, 2H, $OCH_2$), 4.42 (s, 2H, $NCH_2$), 2.73 (s, 6H, $NMe_2$).

Anal. Calcd. for $C_{16}H_{18}ClNOS \cdot HCl$: C, 55.81; H, 5.56; N, 4.07; S, 9.31. Found: C, 55.73; H, 5.59; N, 4.06; S, 9.25.

EXAMPLE 3

Activity Studies

Uptake of $^3$H-Biogenic Amines in Crude Synaptosomal Preparations of Rat Hypothalamus and Striatum.

A 0.5 ml aliquot of a crude synaptosomal preparation prepared according to the technique of Ferris et al., *J. Pharm. Exp. Ther.*, 181, 407 (1972) and Patrick et al., *J. Pharm. Exp. Ther.*, 241, 152 (1987) was incubated in a standard incubation medium containing 10 μM iproniazid, 1 μM ascorbate and 0.1 μM of either $^3$H-dopamine, $^3$H-1-norepinephrine or $^3$-serotonin. Final volumes were 3 mL.

All incubations were conducted for 3 minutes under an atmosphere of 95% $O_2$-5% $CO_2$. The uptake at 0° C. and 37° C. was determined in each experiment and the difference between the two determinations represented the accumulation of $^3$H-amine by the temperature-dependent uptake process. Test compounds were dissolved in the standard incubation medium and preincubated with the crude synaptosomal preparation for 5 minutes, before the addition of the labeled substrate.

Reactions were stopped by the addition of 2 mL of ice-cold 0.32M sucrose containing 25 mM Tris buffer, pH 7.4, and rapid cooling in an ice-bath. Samples were centrifuged at 49,600× g for 10 minutes. The resulting pellet was washed with 5 mL of 0.9% saline and again centrifuged. The washed pellet was resuspended in 2 mL of 0.4N perchloric acid and centrifuged to remove the precipitated protein. A 1 mL aliquot of the supernatant was taken for determination of radioactivity.

TABLE I

| $IC_{50}$ (Molar) for Inhibition of Biogenic Amine Uptake | | | |
|---|---|---|---|
| Compound | Norepinephrine | Dopamine* | Serotonin |
| Example 2 | $5.5 \pm 1.0 \times 10^{-8}$ | 15% at $10^{-5}$ | $2.1 \pm 0.4 \times 10^{-9}$ |

*Percent inhibition is mean of triplicate assay with S.E.M. < ±5%.

EXAMPLE 4

Formulations

A. Tablet

| Ingredient | Amount per Tablet |
|---|---|
| The compound of formula (I) (as the base) | 150 mg |
| Lactose | 85 mg |
| Cornstarch | 50 mg |
| Micronized silica gel | 10 mg |
| Polyvinylpyrrolidone | 5 mg |

The lactose, cornstarch and compound of formula (I) are mixed together and grandulated with a binder (polyvinylpyrrolidone in an alcoholic solution) to form granules. The granules are passed through a 16-20 mesh screen, then air dried, lubricated with micronized silica gel and compressed into tablets. A film coat may then be applied if desired.

B. Capsule

| Ingredient | Amount per Tablet |
|---|---|
| The compound of formula (I) (as the base) | 150 mg |
| Lactose | 125 mg |
| Cornstarch | 125 mg |

The above ingredients are mixed and filled into a two piece hard gelatin capsule.

C. Parenteral Solution

| Ingredient | Amount per Ampule |
|---|---|
| The compound of formula (I) (as a pharmaceutically | 125 mg (calculated as free base) |

| Ingredient | Amount per Ampule |
|---|---|
| acceptable salt) Sterile water for injections, q.s. to | 1.0 mL |

A pharmaceutically acceptable salt of the compound of formula (I) is dissolved in sterile water under sterile conditions to make 1.0 mL. Such a solution may be packaged in a sealed sterile ampule to provide a unit dose or in a sterile vial for multiple doses. If the formulation is to be packed in a multi-dose container, the addition of a bacteriostat such as 0.2 to 0.5% w/v of phenol is desirable.

D. Suppository 150 mg of the hydrochloride salt of the compound of formula (I) is mixed with 250 mg of softened or salted cocoa butter, and a suppository is formed by chilling and shaping in a mold.

We claim:

1. The method of treating depression in a mammal which comprises administering to said mammal an effective antidepressant amount of 5-chloro-2-((2-((dimethylamino)methyl)phenyl)thio)benzyl alcohol or a pharmaceutically acceptable acid addition salt thereof.

2. The method of claim 1 wherein the mammal is a human.

3. The method of treating depression in a mammal which comprises administering to said mammal an effective antidepressant amount of the hydrochloride salt of 5-chloro-2((2-((dimethylamino)-methyl)phenyl)thio)-benzyl alcohol.

4. The method of claim 3 wherein the mammal is a human.

5. The method of inhibiting serotonin uptake in a mammal in need thereof which comprises administering to said mammal an effective serotonin uptake inhibiting amount of 5-chloro-2-((2-((dimethylamino)methyl)phenyl)thio)benzyl alcohol or a pharmaceutically acceptable acid addition salt thereof.

6. The method of claim 5 wherein the mammal is a human.

7. The method of inhibiting serotonin uptake in a mammal in need thereof which comprises administering to said mammal an effective serotonin uptake inhibiting amount of the hydrochloride salt of 5-chloro-2-((2-((dimethylamino)methyl)phenyl)thio)benzyl alcohol.

8. The method of claim 7 wherein the mammal is a human.

9. The method of claim 4 or claim 8 wherein the hydrochloride salt is administered orally.

10. The method of claim 2 where the 5-chloro-2-((2-((dimethylamino)methyl)phenyl)thio)benzyl alcohol or acid addition salt thereof is administered orally in a unit dose of from about 1 mg to 200 mg.

11. The method of claim 2 where the 5-chloro-2-((2-((dimethylamino)methyl)phenyl)thio)benzyl alcohol or acid addition salt thereof is administered orally in a unit dose of from about 5 mg to 100 mg.

12. The method of claim 2 where the 5-chloro-2-((2-((dimethylamino)methyl)phenyl)thio)benzyl alcohol or acid addition salt thereof is administered orally in a unit dose of from about 10 mg to 50 mg.

13. The method of claim 4 where the hydrochloride salt is administered orally in a unit dose of from about 1 mg to 200 mg.

14. The method of claim 4 where the hydrochloride salt is administered orally in a unit dose of from about 5 mg to 100 mg.

15. The method of claim 4 where the hydrochloride salt is administered orally in a unit dose of from about 10 mg to 50 mg.

* * * * *